United States Patent [19]

Kneifel et al.

[11] 4,229,967

[45] Oct. 28, 1980

[54] METHOD AND MEANS FOR TESTING THE FLAMMABILITY OF COMBUSTIBLE MATERIALS

[75] Inventors: Jerome J. Kneifel; John C. Veburg, both of Columbus, Nebr.

[73] Assignee: Dale Electronics, Inc., Columbus, Nebr.

[21] Appl. No.: 972,783

[22] Filed: Dec. 26, 1978

[51] Int. Cl.³ ............................................. G01N 25/00
[52] U.S. Cl. ..................................... 73/15 R; 340/579
[58] Field of Search ..................... 73/15 R; 340/579; 431/13, 25, 59, 78

[56] References Cited

U.S. PATENT DOCUMENTS

| | | | |
|---|---|---|---|
| 2,566,338 | 9/1951 | Kime | 73/15 |
| 3,148,531 | 9/1964 | Stoll et al. | 73/15 |
| 3,301,307 | 1/1967 | Nishigaki et al. | 340/579 |
| 3,302,685 | 2/1967 | Ono et al. | 340/579 |
| 3,665,750 | 5/1972 | Dawn et al. | 73/15 |

*Primary Examiner*—Herbert Goldstein
*Attorney, Agent, or Firm*—Zarley, McKee, Thomte, Voorhees & Sease

[57] ABSTRACT

A method and means for testing the flammability of combustible materials is disclosed with sensor elements for sensing ionization in the vicinity of the material to be tested. The utilization of spaced apart polarized plate elements for sensor elements provides flame detection by sensing the ionization caused by the flame while the alternate utilization of a pair of spaced apart polarized wire elements or sensing elements allows flame height determinations in addition to detecting the presence of a flame.

The method for testing the flammability of a combustible material comprises causing combustion of the material to be tested, sensing ionization in the vicinity of the material and measuring the amount of current flow caused by the ionization. Combustion of the material is selectively, alternatively caused by applying electrical power to the material to cause a flame and applying a heat source to the exterior of the material to externally cause combustion. Ionization is sensed at selective predetermined levels above the material to determine flame height.

18 Claims, 4 Drawing Figures

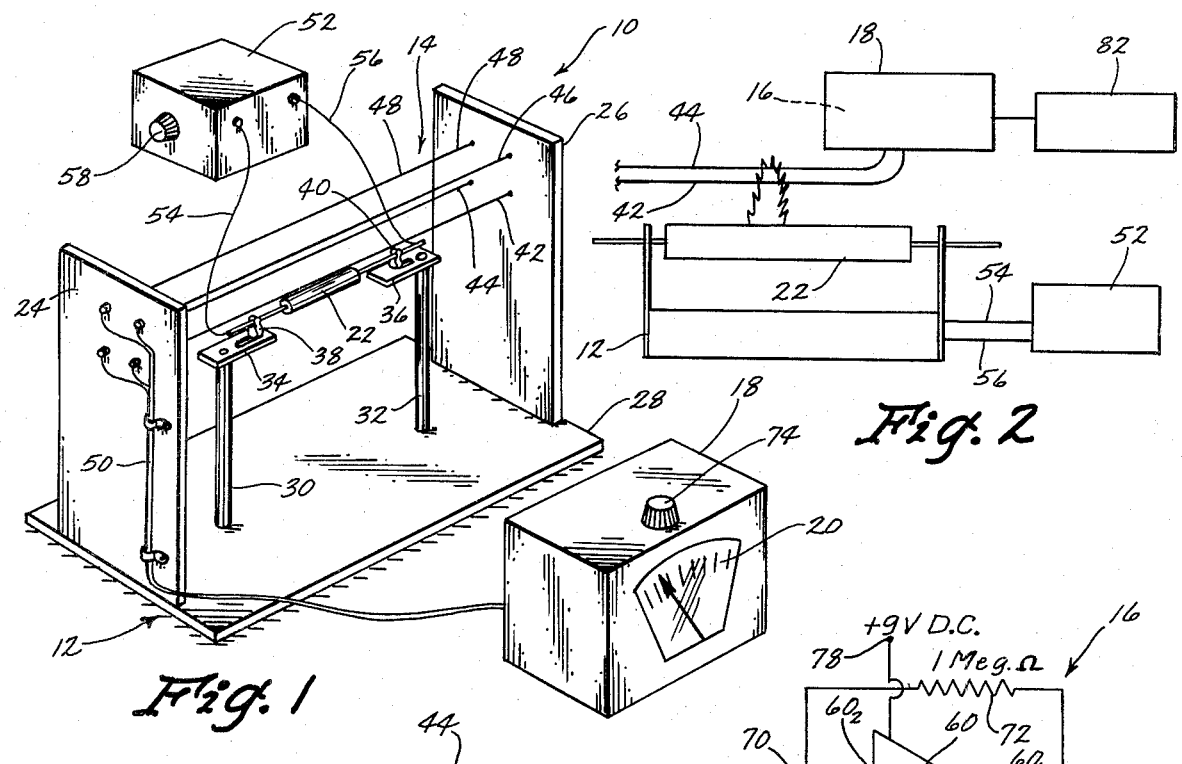
*Fig. 1*
*Fig. 2*
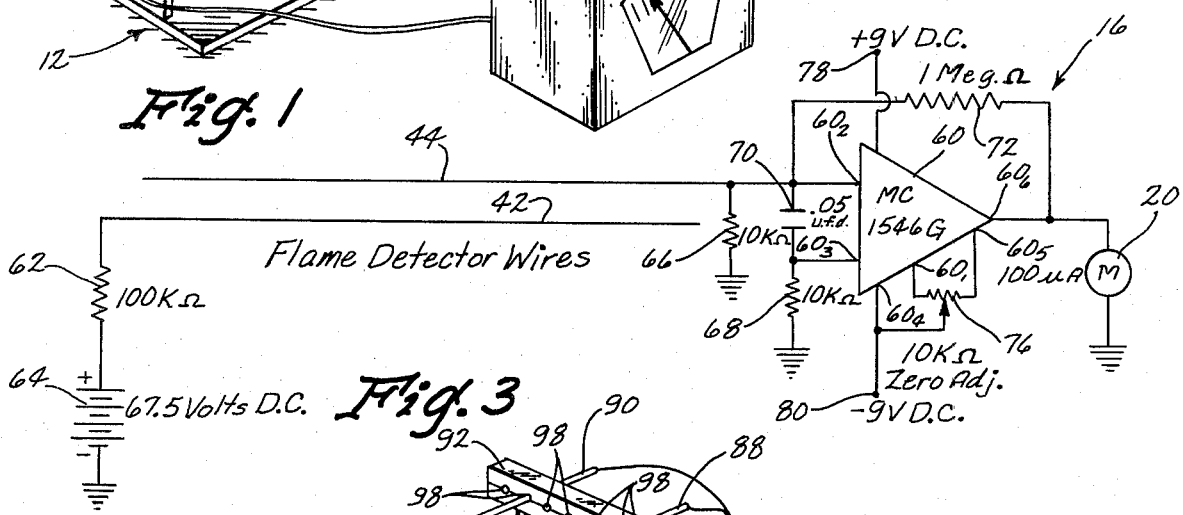
*Fig. 3*
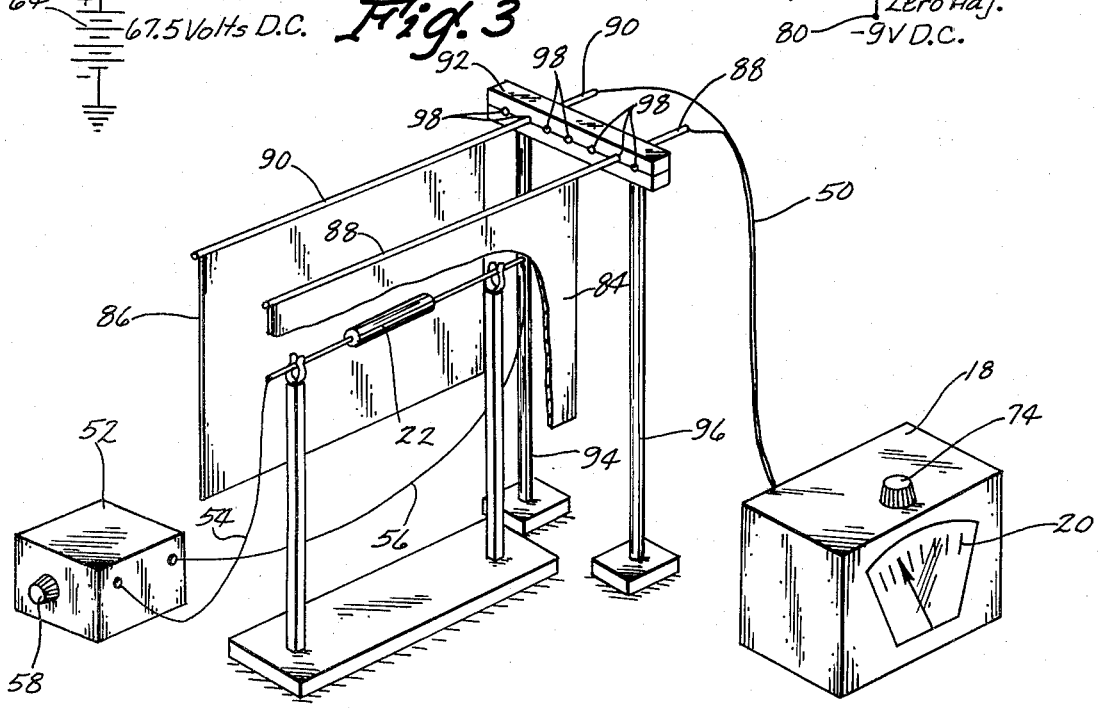
*Fig. 4*

METHOD AND MEANS FOR TESTING THE FLAMMABILITY OF COMBUSTIBLE MATERIALS

BACKGROUND OF THE INVENTION

This invention relates to a method and means for testing the flammability of a material and more particularly to a method and means for detecting the presence of a flame and testing flame height and flame duration.

The flammability characteristics of materials have become important considerations in view of the trends in consumer safety laws and products liability. Generally, flammability tests are intended to determine if a material is either capable of starting a flame or capable of supporting combustion from an external flame source. To determine if a material is capable of starting a flame, a selective amount of electrical power is applied to the material. To determine if a material is capable of supporting combustion, an external flame source such as a bunsen burner is applied to the material for a select interval and then removed. Common testing specification standards include: flame presence per se, flame height and flame duration.

Prior testing devices did not provide an economic and efficient objective means to test the flammability characteristics of materials. Many of the prior flame testing techniques were limited and inaccurate because of the presence of subjective determinations such as flame height and flame duration. Because of the transient nature of flames, subjective determinations are undesirable and an objective testing technique is required. While photography or televising are objective methods for measuring flame height and duration, these methods require development of the film and are expensive.

SUMMARY OF THE INVENTION

A method and means for testing the flammability of a combustible material is disclosed, the means comprising a support element for holding the material to be tested, a sensor element for sensing ionization in the vicinity of the material to be tested, an electronic circuit to detect current flow in the sensor elements, and an indicator for indicating the current flow detected by the electronic circuit. The sensor elements are a pair of polarized spaced apart wire elements positioned a predetermined distance from the material to be tested. An alternate embodiment of the sensor elements is a pair of spaced apart polarized plate elements comprised of a screen material.

The method for testing the flammability of a combustible material comprises causing combustion of the material to be tested, sensing ionization in the vicinity of the material, and measuring the amount of current flow caused by the ionization. Combustion of the material to be tested is alternatively, selectively caused by applying electrical power to the material to cause a flame and applying a heat source to the material to cause the material to support a combustion flame. Further, ionization is sensed at predetermined vertical positions above the material to determine flame height. The time duration of predetermined amounts of current flow caused by ionization is measured to determine the flame duration.

It is a principal object of the present invention to provide an improved and economical objective method and means for testing the flammability of combustible materials.

A still further object of the invention is to provide a testing device to determine the height of a flame.

A still further object of the invention is to provide a testing device for measuring the duration of a flame.

A still further object of the invention is to provide a testing device for detecting the presence of a flame.

A still further object of the invention is to provide a testing device having an indicator to indicate the presence and characteristics of a flame.

A still further object of the invention is to provide a flame testing device that senses ionization caused by a flame and detects the current flow caused by the ionization.

A still further object of the invention is to provide a flame testing device that is efficient and simple in operation.

A still further object of the invention is to provide a flame testing device that is economical to manufacture, durable in use and refined in appearance.

BRIEF DESCRIPTION OF THE DRAWINGS

FIG. 1 is a perspective view of the present invention.
FIG. 2 is a block diagram of the present invention.
FIG. 3 is a schematic diagram of the electronic circuit.
FIG. 4 is an alternate embodiment of the device of FIG. 1.

DESCRIPTION OF THE PREFERRED EMBODIMENT

Numeral 10 generally refers to the device for testing the flammability of combustible materials shown in FIG. 1.

Device 10 is generally comprised of a support assembly 12 for holding the material to be tested, sensor elements 14 for sensing ionization, and electronic circuit 16 being contained in housing 18 for detecting current flow in the sensor elements 14, and an indicator 20 for indicating current flow. For purposes of explanation only, an electrical component 22 is illustrated as the material to be tested in FIG. 1 since electrical components are commonly subjected to flammability tests. However, device 10 can be utilized for testing the flammability of any combustible material.

Support assembly 12 has oppositely disposed side walls 24, 26 securely attached to the bottom support surface 28. Spaced apart upstanding posts 30, 32 are securely attached to support surface 28 and are located between side walls 24, 26. Mounting plates 34, 36 are securely attached to the top of posts 30, 32, respectively. Holder clamps 38, 40 are attached to plates 34, 36 respectively and rigidly hold electrical component 22 therebetween as shown in FIG. 1.

Sensor eements 14 are comprised of a first pair of spaced apart wire elements 42, 44 residing in a common horizontal plane and extending between side walls 24, 26 (FIG. 1). A second pair of spaced apart wire elements 46, 48 are located in a common horizontal plane above wire elements 42, 44 and also extend between side walls 24, 26. Lead wire assembly 50 electrically connects wire elements 42, 44 and 46, 48 to the electronic circuit within housing 18. Component 22 is positioned below the wire elements and centrally disposed therebetween such that any combustion flame supported by the combustion of component 22 will pass between wire elements 42, 44 upon attaining the vertical height of the first pair of elements and will pass between wire elements 46, 48 upon attaining the vertical height of the second pair of elements. Wire elements 42, 44, 46 and 48 are insulated by conventional means (not shown) from side walls 24 and 26.

Electrical power source 52 is electrically connected by lead wires 54, 56 to the opposite ends of component 22. Such conventional power sources are utilized to provide selective quantities of electrical power to the electrical component 22 to cause an internally generated flame. Control knob 58 allows variance of the amount of electrical power applied to the component. The technique of internal generation of flames is a standard flammability testing procedure. The flammability characteristics of materials are additionally alternatively tested by applying an external flame source (not shown) to the component, e.g., a bunsen burner or torch.

Electronic circuit 16 is contained within housing 18 and is schematically shown in FIG. 3. For purposes of simplicity of explanation, only wire elements 42, 44 are schematically depicted in operational electrical connection to circuit 16. It is to be understood, however, that wire elements 46, 48 are connected in a similar configuration and are intended to function in an identical manner. Triangle 60 utilized in electronic circuit 16 is an MC 1546-G operational amplifier manufactured by Motorola Corporation, although other operational amplifiers exhibiting similar characteristics can be utilized with minor circuit variations. For clarity, the particular pins of operational amplifier 60 will be designated by the reference numeral 60 with the pin number in subscript, e.g., $60_5$ represents pin 5 of the amplifier.

Wire elements 42 and 44 are polarized by the series connection of wire element 42 to resistor 62 and battery 64 as shown in FIG. 3. In this configuration, acceptable values are 100 k ohms for resistor 62 and approximately 67.5 volts for battery 64 with resistor 62 being utilized to limit the current and voltage applied to the operational amplifier in the event the sensor wires 42 and 44 become shorted together. Wire element 44 is electrically connected to pin $60_2$ with pin $60_2$ being connected to ground through resistor 66. Pin $60_3$ is connected to ground through resistor 68 and connected to pin $60_2$ by capacitor 70. Pin $60_2$ is connected to pin $60_6$ by resistor 72. Ammeter 20 is connected to pin $60_6$. Potentiometer 76 is electrically connected to pins $60_4$, $60_1$, and $60_5$ as shown in FIG. 3 and is manually adjusted by control knob 74. Potentiometer 76 permits the amplifier output to be set to 0 volts to compensate for leakage currents in the amplifier or in the sensor wires. This zero adjustment is particularly useful where additional electronic circuitry (not shown) is utilized to determine the pass-fail test decision.

Acceptable component values for the particular schematic configuration of FIG. 3 are: 10 k ohms for resistors 66, 68 and rheostat 76; 0.05 microfarids for capacitor 70; 1 meg ohms for resistor 72; 100 microamps for ammeter 20; plus 9 volts for voltage source 78 and minus 9 volts for voltage source 80.

Whenever ionization occurs between the sensor wire elements 42 and 44, the electric field of the sensor elements caused by the polarization thereof directs the ions to one of the wire elements and thereby produces conduction. If the material or component flames, a flame between the sensor elements liberates electrons, i.e., ionization, thereby causing an electron flow between the sensor elements. Ions or electrons produced by the flame are collected by the sensor elements thereby causing a current to flow from battery 64 to the wire element 44 connected to pin $60_2$ of amp 60. This current flow produces a voltage across resistor 66 and this voltage is amplified by operational amp 60 and deflects ammeter 20 to indicate that a flame is present between the wires. Therefore, the presence of a flame between wire elements 42 and 44 is detected by the wire elements and operational amplifier, and indicated by a deflection of the ammeter.

The ability of device 10 to detect the presence of a flame between the wire sensor element allows device 10 to be utilized to measure flame height and flame duration. By noting the vertical distance between the component 22 and the horizontally disposed sensor wire elements 42, 44, a deflection of ammeter 20 indicates a minimum threshhold flame height, i.e., the flame has a vertical height of at least the distance between the component and the wire sensors. To further determine flame height, additional pairs of wire sensor elements may be provided at selective vertical distances above the component 22. As shown in FIG. 1, wire sensor elements 46, 48 are located vertically above wire sensor elements 42, 44 and allow device 10 to detect the presence of a flame at this selected vertical height. This additional pair of sensor elements can thereby be utilized to indicate a second minimum threshhold flame height or to more particularly determine the actual flame height present. The utilization of multiple sensor elements requires additional circuitry to support the additional elements. The schematic of FIG. 3 provides the circuitry for a single pair of wire sensor elements.

The duration of a flame can also be determined with device 10 by the addition of a timing circuit 82 to the operational amplifier 60 of FIG. 3. A conventional timing circuit electrically connected to electronic circuit 16 would allow the timing of flame presence as detected by wire sensor elements 42, 44 and operational amplifier 60, and thereby measure flame duration. A conventional chart recorder (not shown) may also be connected to electronic circuit 16 to provide a visual record of flame detection and flame duration. Additionally, an alarm indicator such as an audio alarm, a visual alarm, etc. can be electrically connected to circuit 16 to provide an audio or visual indication of flame detection and flame height. A conventional alarm indicator is intended to be shown in the block diagram of FIG. 3 as included within timing circuit 82.

While two stationary pairs of wire sensor elements are shown in FIG. 1, the vertical distance between one pair of wire sensor elements and the component can be selectively adjustable to test flame height characteristics. One pair of wire sensor elements can be vertically movably mounted relative to the stationary position of component 22 to provide adjustability. Alternatively, mounting plates 34 and 36 may be vertically adjustably mounted to upstanding posts 30 and 32, respectively, to also allow vertical height adjustment of component 22 relative to the wire sensor elements.

An alternate embodiment of sensor elements 14 is shown in FIG. 4 and comprises a pair of spaced apart plate elements 84 and 86. Mounting rods 88 and 90 are attached to the upper edges of plates 84 and 86 respectively and are detachably secured in spaced apart parallel relation about component 22 by mounting frame 92.

Mounting frame 92 is securely attached to support posts 94, 96 and contains a plurality of apertures 98 therethrough to retentively receive rods 88 and 90 in selective spaced apart disposition as shown in FIG. 4. Lead wire assembly 50 electrically connects electronic circuit 16 to plates 84 and 86. Plates 84 and 86 are polarized in a manner similar to wire elements 42 and 44. Polarized plate elements 84 and 86 sense ionization caused by a flame from component 22 in a manner similar to the aforedescribed wire elements 42 and 44. Plate elements 84 and 86 can be utilized to detect a flame and to determine flame duration. However, plates 84 and 86 cannot be utilized to detect flame height because of the plate like construction. Alternatively, plate elements 84 and 86 may be constructed of a screen material.

Thus, device 10 provides a method and means for performing various flammability tests on combustible materials to determine if the material is capable of starting a flame or capable of supporting combustion from an external flame source. Device 10 provides an objective means to detect the presence of a flame and to determine both flame duration and flame height. Thus, it can be seen that this device accomplishes at least all of its stated objectives.

What is claimed is:

1. A device for testing the flammability of a combustible material, comprising,
    means for holding the material to be tested,
    means for sensing ionization in the vicinity of the material to be tested, said means for sensing comprising a pair of spaced-apart polarized sensor elements,
    means for supporting said sensor elements in spaced-apart relation to the material to be tested and at positions above and on opposite sides of said material whereby a flame supported by the combustion of said material will pass between said sensor elements,
    circuit means to detect current flow in said means for sensing ionization, said circuit means being electrically connected to said sensing means, and
    indicator means for indicating current flow detected by said circuit means, said indicator means being electrically connected to said circuit means.

2. The device of claim 1 wherein said means for sensing ionization comprises a pair of spaced apart polarized wire elements and sensing ionization between said pair of sensor elements.

3. The device of claim 1 wherein said means for sensing ionization comprises a pair of spaced apart polarized plate elements.

4. The device of claim 3 wherein said plate elements are constructed of a screen material.

5. The device of claim 1 further comprising means for applying electrical power to the material to be tested to cause combustion, said means for applying electrical power being adapted for electrical connection to the material to be tested.

6. The device of claim 1 further comprising means for generating an external flame for application to the material to be tested.

7. The device of claim 1 wherein said circuit means comprises an operational amplifier means and said indicator means is an ammeter electrically connected to said operational amplifier means so that a flow of current in said means for sensing ionization causes deflection of said ammeter.

8. The device of claim 1 wherein said indicator means comprises an alarm electrically connected to said circuit means so that a predetermined amount of current flow detected by said circuit means activates said alarm.

9. The device of claim 1 wherein said indicator means comprises a chart recorder.

10. The device of claim 1 wherein the relative vertical position of said means for sensing ionization and said means for holding the material to be tested is vertically adjustable.

11. The device of claim 1 wherein said means for holding the material to be tested is vertically adjustable relative to said means for sensing ionization.

12. The device of claim 1 wherein said means for sensing ionization is vertically adjustable relative to said means for holding the material.

13. The device of claim 1 wherein said means for sensing ionization comprises a first pair of spaced apart polarized wire elements disposed at a first predetermined vertical position above the material to be tested.

14. The device of claim 13 wherein said means for sensing ionization further comprises a second pair of spaced apart polarized wire elements disposed at a second predetermined vertical position above the material to be tested.

15. The device of claim 13 wherein said first pair of polarized wire elements are arranged in a common horizontal plane.

16. A method for testing the flammability of a combustible material, comprising,
    causing combustion of the material to be tested,
    providing a pair of electrically conductive sensor elements,
    arranging said sensor elements above and on opposite sides of the material to be tested whereby a combustion flame supported by the combustion of said material will pass between said sensor elements.

17. The method of claim 16 further comprising arranging said pair of sensor elements in a common horizontal plane.

18. The method of claim 16 further comprising
    indicating the occurrence of predetermined amounts of current
    flow caused by ionization.

* * * * *